(12) United States Patent
Samain et al.

(10) Patent No.: US 6,511,651 B1
(45) Date of Patent: Jan. 28, 2003

(54) AEROSOL DEVICE BASED ON ALCOHOLIC COMPOSITIONS OF FIXING MATERIALS COMPRISING VINYLLACTAM UNITS

(75) Inventors: Henri Samain, Bievres (FR); Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/976,506

(22) Filed: Nov. 24, 1997

(30) Foreign Application Priority Data

Nov. 22, 1996 (FR) .............................. 96 14330

(51) Int. Cl.⁷ ................................. A61L 9/04
(52) U.S. Cl. .................. 424/45; 424/70.1; 424/70.2; 424/70.12; 424/70.15; 424/70.16
(58) Field of Search .................. 424/45, 70.1, 70.2, 424/70.12, 70.15, 70.16

(56) References Cited

U.S. PATENT DOCUMENTS 4,049,007 A * 9/1977 Russell et al. ................ 132/7
4,983,377 A * 1/1991 Murphy et al. ............... 424/47

FOREIGN PATENT DOCUMENTS

| DE | 4 414 423 | 11/1995 |
| DE | 4 414 424 | 11/1995 |
| EP | 205306 | * 6/1986 |
| WO | WO 95/00105 | 1/1995 |
| WO | WO 95/33437 | 12/1995 |

OTHER PUBLICATIONS

English Language Derwent Abstract of DE 4 414 423. Nov. 2, 1995.
English Language Derwent Abstract of DE 4 414 424 Nov. 2, 1995.

* cited by examiner

*Primary Examiner*—Thurman K. Page
*Assistant Examiner*—Lakshmi Channavajjala
(74) *Attorney, Agent, or Firm*—Finnegan, Henderson, Farabow, Garrett & Dunner, LLP

(57) ABSTRACT

An aerosol device comprising a container containing an aerosol composition, comprising, on the one hand, a liquid phase (or fluid) containing at least one fixing material in a suitable solvent and, on the other hand, a propellant, and a means for distributing the aerosol composition, the fixing material having a glass transition temperature (Tg) of greater than or equal to 40° C., the fixing material comprising at least one polymer containing vinyllactam units, and the device being suitable for obtaining a wetting power of greater than or equal to 40 mg/s. The invention also relates to a process for treating keratin fibres, in which a composition comprising a fixing material having a glass transition temperature (Tg) of greater than or equal to 40° C., this fixing material comprising at least one polymer containing vinyllactam units, is applied to the fibres by means of a suitable device in order to obtain a wetting power of greater than or equal to 40 mg/s.

21 Claims, No Drawings

AEROSOL DEVICE BASED ON ALCOHOLIC COMPOSITIONS OF FIXING MATERIALS COMPRISING VINYLLACTAM UNITS

The present invention relates to novel aerosol devices intended to fix the hair.

The hair products for shaping and/or holding the hairstyle which are the most widely available on the cosmetics market are spray compositions comprising a solution, usually an alcoholic or aqueous solution, and one or more materials, generally polymer resins, whose function is to form welds between individual hairs, these materials also being known as fixing materials, mixed with various cosmetic adjuvants. These solutions are generally packaged either in a suitable aerosol container placed under pressure with the aid of a propellant or in a pump-dispenser bottle.

Many aerosol systems intended to fix the hair are known, these systems containing, on the one hand, a liquid phase (or fluid) and, on the other hand, a propellant. The liquid phase contains the fixing materials and a suitable solvent. The function of the propellant is to provide a pressure which allows the liquid phase to be sprayed and to be applied to the hair in the form of a cloud of dispersed droplets. It is after the liquid phase has been applied to the hair that it dries, allowing the formation of welds which are necessary for fixing the hair, by means of the fixing materials.

It is desirable that the welds be rigid enough to ensure that the hair is held in place. However, it is also desired that they be fragile enough for the user to be able to destroy them by combing or brushing the hair, without damaging the scalp or the hair.

The fixing materials are generally fixing polymers, that is to say film-forming polymers that are soluble or dispersible in water and in alcohol, such as vinyl acetate/crotonic acid copolymers and anionic or amphoteric acrylic resins. These materials make it possible readily to obtain the fixing effect but, on the other hand, under the usual conditions of lacquering, the hair looks stiff and has a coarse or even sticky feel and is often difficult to disentangle after brushing or combing.

These drawbacks are linked to several parameters, among which mention may be made of the nature of the fixing polymer(s), or alternatively the nature of the welds. To overcome these drawbacks, it is thus possible to act on these two parameters without, however, diminishing the desired fixing effect. To improve the cosmetic properties of the fixing materials, it has been proposed to combine different polymers, for example as discussed in documents WO 94/12148, WO 96/06592 and U.S. Pat. No. 5,158,762, the disclosures of which are specifically incorporated by reference herein.

The inventors have found that by appropriately selecting, on the one hand, the fixing polymers and, on the other hand, the diffusion parameters for the compositions, it is possible to act on the quality of the welds while at the same time retaining good fixing and/or hair shaping qualities, and thus to provide excellent cosmetic properties such as softness and disentangling.

The aerosol device according to the invention comprises a container containing an aerosol composition comprising, on the one hand, a liquid phase (or fluid) containing at least one fixing material in a suitable solvent and, on the other hand, a propellant, and a means for distributing the aerosol composition, the fixing material having a glass transition temperature (Tg) of greater than or equal to 40° C., the fixing material comprising at least one polymer containing vinyllactam units, and the device being suitable for obtaining a wetting power of greater than or equal to 40 mg/s.

The distribution means generally comprises a distribution valve controlled by a distribution head, itself comprising a nozzle through which the aerosol composition is vaporized.

The terms "Tg" and "wetting power" as understood according to the present invention are defined below.

According to the present invention, the expression glass transition temperature (Tg) is understood to refer to the Tg of the fixing material in the dry extract, the dry extract comprising all of the non-volatile materials in the fluid, or solids.

According to the present invention, the wetting power corresponds to the amount of product received by a sheet of plastic placed 35 cm away from the nozzle of the aerosol device over a given unit of time. The product then comprises the solids plus some of the solvent which has not evaporated over the trajectory plus, possibly, some of the non-evaporated propellant. This wetting power is expressed in mg/s and is measured according to the invention by the following method:

a sheet of plastic 21 cm×23 cm in size is suspended vertically on a precision balance ($1/1000$), the sheet being connected to the balance via the upper edge (generally by means of a balance hook inserted into a perforation placed at the center of the width and 1 cm from the upper edge of the sheet), and is kept vertical by applying a weight centered on the lower edge (generally by means of a clip fixed to and centered on the lower edge);

a block is placed behind the lower edge of the sheet in order to keep the sheet vertical during impacting of the product;

the aerosol device is placed vertically such that the composition diffusion nozzle is arranged at the center and 35 cm away from the vertical sheet, to allow vaporization of the product perpendicular to the sheet;

the composition is vaporized for 5 seconds; and the amount of product received on the vertical sheet is measured once the vaporization is complete.

For greater precision, a suitable device comprising a support means for the aerosol device and means for allowing three-dimensional adjustment of the position of the nozzle relative to the vertical sheet may be used. This device may also be equipped with a pneumatic spray-control (firing and duration) device, so as to control the duration of the vaporization precisely. The whole assembly may be controlled by computer.

To avoid any environmental interference, the trajectory of the product between the nozzle and the sheet will advantageously be protected horizontally and vertically by the walls of a tunnel of suitable size.

Lastly, the product is advantageously vaporized under a controlled atmosphere, preferably at a temperature of 20° C. and at a relative humidity of 40%.

Preferably, the fixing material has a Tg of greater than or equal to 60° C.

Advantageously, the fixing material comprises polymers containing vinyllactam units, alone or in combination with common cosmetic additives, for example plasticizers.

According to the invention, the polymers containing vinyllactam units are those which comprise units of formula

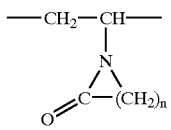

in which n is, independently, 3, 4 or 5.

The polymers containing vinyllactam units are advantageously copolymers or may also comprise units of formula

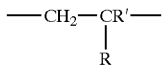

in which:

R represents, independently, a carboxyl radical, a carbalkoxy radical, an acyloxy radical, it being possible for the alkoxy group of the carbalkoxy radical to be substituted with at least one hydroxyl, amino, alkylamino or dialkylamino radical, or an aryl radical, in particular phenyl, optionally substituted with at least one alkyl radical, and R' represents a hydrogen atom or an alkyl radical.

According to the invention, the term alkyl is preferably understood to denote linear or branched $C_1$–$C_{10}$ alkyl radicals, more preferably $C_1$–$C_4$ alkyl radicals, in particular the methyl, ethyl, n-propyl, i-propyl, n-butyl and t-butyl radicals.

According to the invention, the term acyl is preferably understood to refer to acyl radicals in which the alkyl residue is a linear or branched $C_1$–$C_{10}$ alkyl, in particular the acetyl or propionyl radicals.

The polymers containing vinyllactam units according to the invention are preferably nonionic or weakly cationic polymers. They are described, in particular, in U.S. Pat. Nos. 3,770,683, 3,929,735, 4,521,404, 5,158,762 and 5,406,315, and in International patent applications WO 94/121148, WO 96/06592 and WO 96/10593, the disclosures of each of which are specifically incorporated by reference herein. These polymers may be in pulverulent form or in the form of a solution or a suspension.

Among the polymers containing vinyllactam units which are useful according to the invention, mention will be made more particularly of polyvinylpyrrolidones, polyvinylcaprolactams, polyvinylpyrrolidone/vinyl acetate copolymers, polyvinylpyrrolidone/non-quaternized diaminoethyl methacrylate copolymers (marketed in particular under the names Copolymer 845, Copolymer 958 and Copolymer 937 by the company ISP), polyvinylpyrrolidone/vinyl acetate/vinyl propionate terpolymers (marketed in particular under the name Luviskol VAP 343 by the company BASF), vinylcaprolactam/vinylpyrrolidone/dimethylaminoethyl methacrylate terpolymers with a Tg of about 170° C. (marketed in particular under the names Gaffix VC 713, $H_2$OLD, ACP 1187 and ACP 1189 by the company ISP) and (meth)acrylic acid/(meth)acrylates/vinylpyrrolidone terpolymers (marketed in particular under the names Stepanhold Extra by the company Stepan, Luvimer VBM 35 and Luvimer VBM 70 by the company BASF).

The polymers containing vinyllactam units which are useful according to the invention are preferably rapid-rigidifying polymers. According to the invention, the expression rapid-rigidifying polymers is understood to refer to polymers which lead to rigid welds in less than 10 minutes.

The number-average molecular mass of the polymer containing vinyllactam units is generally greater than approximately 5000, preferably approximately ranging from 10,000 to 1,000,000, more preferably approximately from 10,000 to 100,000.

The fixing material may be used in dissolved form or in the form of dispersions of solid polymer particles.

Advantageously, the aerosol device according to the invention is suitable for obtaining a wetting power ranging from 40 mg/s to 400 mg/s.

According to a preferred embodiment of the invention, the aerosol device is suitable for obtaining a flow rate of solids of greater than or equal to 20 mg/s, and preferably ranging from 20 mg/s to 60 mg/s.

According to the present invention, the solids flow rate ($D_{SM}$) corresponds to the amount of dry extract which leaves the aerosol device per unit of time. This solids flow rate is expressed in mg/s and is calculated by multiplying the solids concentration in the aerosol composition ($C_{SM}$) by the flow rate of the aerosol composition at the nozzle outlet ($D_{AC}$):

$$D_{SM} = C_{SM} \times D_{AC}.$$

The solids concentration in the aerosol composition ($C_{SM}$) corresponds to the amount of solids relative to 100 g of aerosol composition (fluid+propellant). The solids concentration is expressed as a percentage and is measured after spraying by evaporation of the volatile components of the spray residue for 1 hour 30 at 105° C.

The flow rate of the aerosol composition ($D_{AC}$) corresponds to the amount of aerosol composition (fluid+propellant) leaving the aerosol device per unit of time. It is expressed in mg/s and is measured by the difference between the weight of aerosol before ($M_0$) and after ($M_1$) vaporization for 10 seconds:

$$D_{AC} = (M_0 - M_1)/10.$$

The solids flow rate and wetting power characteristics of the aerosol devices according to the invention depend, on the one hand, on the aerosol composition and, on the other hand, on the means of distribution, the two needing to be suitable in order to obtain the desired characteristics. Among the parameters which may influence these characteristics, mention will be made more particularly of the solids concentration ($C_{SM}$), the flow rate of aerosol composition ($D_{AC}$) and the phase of the aerosol composition.

The solids concentration ($C_{SM}$) ranges advantageously from 2.5 to 15% by weight relative to the total weight of the aerosol composition (fluid+propellant), and preferably from 3.5 to 10% by weight.

The flow rate of aerosol composition ($D_{AC}$) will thus be suitable to obtain a flow rate of solids ($D_{SM}$) as defined above. The $D_{AC}$ will preferably range from 400 to 800 mg/s, more preferably close to 600 mg/s.

The phase of the aerosol composition is preferably a long phase, that is to say that the fluid/propellant weight ratio is greater than 1/1, more preferably ranging from 1.2/1 to 3/1.

The appropriate solvent advantageously contains at least 40% by volume of alcohol, preferably at least 70% by volume of alcohol. According to the invention, the term alcohol is understood to refer to a $C_1$–$C_4$ aliphatic alcohol, preferably ethanol. This may be, for example, an aqueous-alcoholic solvent comprising at least 40% by volume of alcohol.

The propellant comprises the compressed or liquefied gases usually used for the preparation of aerosol compositions. Air, carbon dioxide or nitrogen, these being compressed, or a gas which is soluble or insoluble in the composition, such as dimethyl ether, fluoro or non-fluoro hydrocarbons, and mixtures thereof, are preferably used.

The aerosol composition according to the invention may also comprise other fixing polymers provided that they do not alter the characteristics of the device according to the invention, in particular as regards the Tg value of the fixing material. These fixing polymers are, in particular, acrylic acid copolymers such as acrylic acid/ethyl acrylate/N-tert-butylacrylamide terpolymer, marketed under the name Ultrahold Strong by the company BASF, crotonic acid/vinyl acetate/vinyl t-butylbenzoate terpolymer, the methacrylic acid/ethyl acrylate/t-butyl acrylate terpolymer marketed under the name Luvimer 100P by the company BASF, or alternatively grafted silicone polymers containing a polysiloxane skeleton grafted with at least one anionic hydrocarbon radical, described in particular in patent applications EP-A-0,582,152, WO 93/23009 and WO 95/03776, the disclosures of which are specifically incorporated by reference herein, such as silicone polymers containing in their structure the unit of formula (I) below:

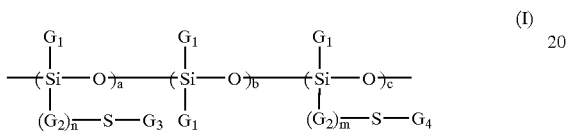

(I)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 40; b is an integer ranging from 10 to 340, c is an integer ranging from 0 to 40; with the proviso that one of the parameters a and c is other than 0. More particularly, the anionic grafted silicone polymers containing a polysiloxane skeleton grafted with at least one anionic hydrocarbon radical disclosed in the copending U.S. patent application entitled "Aerosol Device Based on Alcohol Compositions of Fixing Materials Comprising Anionic Grafted Silicone Polymers," filed the same day as the present application and in the name of the same inventors of the present application, the disclosure of which is specifically incorporated herein by reference, can be advantageously used in accordance with the present invention.

Depending on the aerosol composition (fluid+propellant), a person skilled in the art will know how to select the appropriate distribution means in order to obtain the desired flow rate of solids and wetting power characteristics.

The specific characteristics defined above, solids concentration ($C_{SM}$) and phase, may be obtained by selecting the appropriate distribution means and/or by modifying the formulation.

The appropriate valves for the above specific compositions are, in particular, straight-line valves with a spray nozzle having a diameter ranging from 0.35 to 0.60 mm, preferably from 0.40 to 0.40 mm, advantageously without internal restriction or an additional gas connection. These are, in particular, valves marketed under the name Coster T104 RA36/0/4 by the company Coster or the Precision Experimental 15130 valve comprising a spray nozzle and a valve body 0.46 mm in diameter without an additional gas connection, from the company Precision.

The appropriate diffusers for the above specific compositions are, in particular, push-buttons marketed under the name Precision 216903-40AD29 by the company Precision.

The present invention also relates to a process for treating keratin fibres, in which a composition comprising a fixing material having a glass transition temperature (Tg) of greater than or equal to 40° C. comprising at least one polymer containing vinyllactam units as defined above is applied to the fibres by means of a suitable device in order to obtain a wetting power of greater than or equal to 40 mg/s.

The examples below illustrate the invention without, however, limiting its scope. In the examples, "AM" means "active material".

EXAMPLE 1

Importance of the "Wetting Power" for Lacquering

The following two aerosol devices were prepared:
Device 1 (According to the Invention)
    The following fluid was prepared:
Composition A

| | |
|---|---|
| Vinylcaprolactam/vinylpyrrolidone/dimethyl-aminoethyl methacrylate terpolymer marketed under the name Gaffix VC 713 by the company ISP | 6.0 g AM |
| Tripropylene glycol monomethyl ether marketed under the name Dowanol TPM by the company Dow Chemical | 0.06 g |
| Silicone marketed under the name DC 190 Fluid by the company Dow Corning | 0.30 g |
| Ethanol qs | 100.00 g |

65 g of this fluid were introduced into an aerosol can which was fitted with a Precision Experimental 15130 valve and 35 g of dimethyl ether as propellant and a Precision 216903-40AD29 push-button were then added.

The characteristics of this device were as follows:
    Tg of the fixing material: 61° C.
    Wetting power: 110 mg/s.
Device 2 (Comparative)
    The following fluid was prepared:
Composition B

| | |
|---|---|
| Vinylcaprolactam/vinylpyrrolidone/dimethyl-aminoethyl methacrylate terpolymer marketed under the name Gaffix VC 713 by the company ISP | 9.0 g AM |
| Tripropylene glycol monomethyl ether marketed under the name Dowanol TPM by the company Dow Chemical | 0.09 g |
| Silicone marketed under the name DC 190 Fluid by the company Dow Corning | 0.45 g |
| Ethanol qs | 100.00 g |

37 g of this fluid and 20 g of pentane were introduced into an aerosol can which was fitted with a Precision P155/S90 valve (marketed by the company Precision) and 43 g of dimethyl ether as propellant and a Precision 21 6943-40 push-button (marketed by the company Precision) were then added.

The characteristics of this device were as follows:
    Tg of the fixing material: 61° C.
    Wetting power: 30 mg/s.
    These two devices were tested on ten heads by half-head testing. In all cases, the tests showed that only the side treated by the device according to the invention made it possible to obtain the desired cosmetic fixing effect. On the other hand, device 2 (comparative) did not make it possible to obtain a satisfactory cosmetic fixing result.

EXAMPLE 2

Importance of the "Tg" for Obtaining Good Cosmetic Properties

The following fluids were prepared:
Composition C

| | |
|---|---|
| Vinylcaprolactam/vinylpyrrolidone/dimethyl-aminoethyl methacrylate terpolymer marketed under the name Gaffix VC 713 by the company ISP | 6.0 g AM |
| Ethanol qs | 100.00 g |

Composition D

| | |
|---|---|
| Vinylcaprolactam/vinylpyrrolidone/dimethyl-aminoethyl methacrylate terpolymer marketed under the name Gaffix VC 713 by the company ISP | 6.0 g AM |
| Tripropylene glycol monomethyl ether marketed under the name Dowanol TPM by the company Dow Chemical | 2.40 g |
| Ethanol qs | 100.00 g |

Aerosol devices 3 and 4 were prepared by introducing 65 g of compositions C and D, respectively, into separate aerosol cans. The two cans were fitted with a Precision Experimental 15130 valve and 35 g of dimethyl ether as propellant and a Precision 216903-40AD29 push-button were then added.

For the two devices, the wetting power was 110 mg/s.

The Tg values of the fixing materials in the two devices were as follows:

Tg device 3 (according to the invention): 61° C.

Tg device 4 (comparative): 29° C.

The performance levels of the two devices were compared by spraying the two compositions on ten heads by half-head testing. In all cases, the fixing powers were satisfactory and comparable. However, the side of the head treated with device 3 according to the invention felt more pleasant than the side treated with the comparative device 4, and similarly the disentangling was easier on that same side, and the feel after disentangling was also considered to be more pleasant.

EXAMPLE 3

Devices According to the Invention

The following fluids were prepared:
Composition E

| | |
|---|---|
| Vinylcaprolactam | 7.0 g AM |
| Ethanol qs | 100.00 g |

Composition F

| | |
|---|---|
| Vinylcaprolactam/vinylpyrrolidone/dimethyl-aminoethyl methacrylate terpolymer marketed under the name Gaffix VC 713 by the company ISP | 4.0 g AM |
| Acrylic acid/ethyl acrylate/N-tert-butylacrylamide terpolymer marketed under the name Ultrahold Strong by the company BASF | 2.0 g AM |
| Ethanol qs | 100.00 g |

Aerosol devices 5 and 6 according to the invention were prepared by introducing 65 g of the compositions E and F, respectively, into separate aerosol cans. The two cans were fitted with a Precision Experimental 15130 valve and 35 g of dimethyl ether as propellant and a Precision 216903-40AD29 push-button were then added.

These two devices according to the invention made it possible to obtain the cosmetic fixing, feel and disentangling results in accordance with the invention.

We claim:

1. An aerosol device comprising:
   a container containing an aerosol composition, said aerosol composition comprising a liquid phase or fluid containing at least one fixing material in a suitable solvent and a propellant, wherein said at least one fixing material has a glass transition temperature (Tg) of greater than or equal to 40° C. and comprises at least one polymer containing vinyllactam units; and
   a means for distributing said aerosol composition wherein said device is suitable for obtaining a wetting power of greater than or equal to 40 mg/s.

2. A device according to claim 1, wherein said at least one fixing material consists essentially of at least one polymer containing vinyllactam units.

3. A device according to claim 1, wherein said at least one polymer containing vinyllactam units comprises units of formula

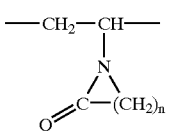

wherein n is, independently, 3, 4 or 5.

4. A device according to claim 1, wherein said at least one polymer containing vinyllactam units is a copolymer further comprising units of formula

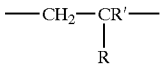

wherein:
   R represents, independently, a carboxyl radical, a carbalkoxy radical or an acyloxy radical, it being possible for the alkoxy group of the carbalkoxy radical to be substituted with at least one hydroxyl, amino, alkylamino, dialkylamino or aryl radical, and
   R' represents, independently, a hydrogen atom or an alkyl radical.

5. A device according to claim 4 wherein said aryl radical is a phenyl radical, optionally substituted with at least one alkyl radical.

6. A device according to claim 1, wherein said at least one polymer containing vinyllactam units is a polyvinylpyrrolidone, polyvinylcaprolactam, polyvinylpyrrolidone/vinyl acetate copolymer, polyvinylpyrrolidone/non-quaternized diaminoethyl methacrylate copolymer, polyvinylpyrrolidone/vinyl acetate/vinyl propionate terpolymer, vinylcaprolactam/vinylpyrrolidone/dimethylaminoethyl methacrylate terpolymer or a (meth)acrylic acid/(meth)acrylates/vinylpyrrol idone terpolymer.

7. A device according to claim 1, wherein said device is suitable for obtaining a wetting power ranging from 40 mg/s to 400 mg/s.

8. A device according to claim 1, wherein said fixing material comprises a dispersion of solid polymer particles and wherein said device is suitable for obtaining a flow rate of solids greater than or equal to 20 mg/s.

9. A device according to claim 8, wherein said flow rate of solids ranges from 20 to 60 mg/s.

10. A device according to claim 1, wherein the solids concentration ($C_{SM}$) ranges from 2.5 to 15% by weight relative to the total weight of the aerosol composition (fluid+propellant).

11. A device according to claim 10, wherein said solids concentration ($C_{SM}$) ranges from 3.5 to 10% by weight.

12. A device according to claim 1, wherein the flow rate of said aerosol composition ($D_{AC}$) ranges from 400 to 800 mg/s.

13. A device according to claim 12, wherein said flow rate of said aerosol composition ($D_{AC}$) is approximately equal to 600 mg/s.

14. A device according to claim 1, wherein the fluid/propellant weight ratio in said composition is greater than 1/1.

15. A device according to claim 14, wherein said fluid/propellant weight ratio in said composition ranges from 1.2/1 to 3/1.

16. A device according to claim 1, wherein said suitable solvent contains at least 40% by volume of alcohol.

17. A device according to claim 16, wherein said suitable solvent contains at least 70% by volume of alcohol.

18. A device according to claim 1, wherein said aerosol composition further comprises at least one additional fixing polymer.

19. A device according to claim 1, wherein said fixing material has a glass transition temperature (Tg) of greater than or equal to 60° C.

20. A device according to claim 1, wherein said at least one polymer containing vinyllactam units is a rapid-rigidifying polymer.

21. A process for treating keratin fibres, said process comprising applying to said fibres, by means of a suitable device in order to obtain a wetting power of greater than or equal to 40 mg/s, a composition comprising a fixing material having a glass transition temperature (Tg) of greater than or equal to 40° C., said fixing material comprising at least one polymer containing vinyllactam units.

* * * * *